United States Patent
Black et al.

(10) Patent No.: US 8,389,510 B2
(45) Date of Patent: Mar. 5, 2013

(54) CRYSTALLINE FORMS

(75) Inventors: Simon N. Black, Cheshire (GB); Simon D. Broady, Cheshire (GB); Alan S. Kirschner, Wilmington, DE (US); James A. Osborn, Wilmington, DE (US); Stewart D. Jolly, Bristol (GB); Dan B. Brown, Wilmington, DE (US); Daniel Korey, Wilmington, DE (US); Karen B. Main, Wilmington, DE (US); Richard J. R. Creekmore, Wilmington, DE (US); Jean M. Surian, Wilmington, DE (US); Vivian Y. Bi, Wilmington, DE (US); Peter Bernstein, Wilmington, DE (US); James B. Campbell, Wilmington, DE (US); Greg Christoph, Wilmington, DE (US); Scott W. Grimm, Wilmington, DE (US); Dan Widzowski, Wilmington, DE (US); James Hulsizer, Wilmington, DE (US); Phil Edwards, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 187 days.

(21) Appl. No.: 12/726,619

(22) Filed: Mar. 18, 2010

(65) Prior Publication Data

US 2011/0237568 A1 Sep. 29, 2011

Related U.S. Application Data

(63) Continuation-in-part of application No. 12/093,956, filed as application No. PCT/US2006/061071 on Nov. 18, 2006, now abandoned, application No. 12/726,619, which is a continuation-in-part of application No. 12/093,952, filed as application No. PCT/US2006/061069 on Nov. 18, 2006, now abandoned, application No. 12/726,619, which is a continuation-in-part of application No. 12/093,954, filed as application No. PCT/US2006/061070 on Nov. 18, 2006, now abandoned, application No. 12/726,619, which is a continuation-in-part of application No. 12/093,957, filed as application No. PCT/US2006/061072 on Nov. 18, 2006, now abandoned, application No. 12/726,619, which is a continuation-in-part of application No. 12/520,133, filed as application No. PCT/US2007/088036 on Dec. 19, 2007, now abandoned, application No. 12/726,619, which is a continuation-in-part of application No. 12/531,717, filed as application No. PCT/US2008/057808 on Mar. 21, 2008, now abandoned, application No. 12/726,619, which is a continuation-in-part of application No. 12/520,152, filed as application No. PCT/US2007/088040 on Dec. 19, 2007, now abandoned, application No. 12/726,619, which is a continuation-in-part of application No. 12/520,162, filed as application No. PCT/US2007/088053 on Dec. 19, 2007, now abandoned, application No. 12/726,619, which is a continuation-in-part of application No.

(Continued)

(51) Int. Cl.
*A61P 25/18* (2006.01)
*A61K 31/554* (2006.01)
*C07D 281/02* (2006.01)
(52) U.S. Cl. .................................. 514/211.13; 540/551
(58) Field of Classification Search ............ 514/211.13; 540/551
See application file for complete search history.

(56) References Cited

U.S. PATENT DOCUMENTS

| | | | |
|---|---|---|---|
| 3,539,573 A | 11/1970 | Hunziker et al. | |
| 3,755,340 A | 8/1973 | Hoehn et al. | |
| 4,097,597 A | 6/1978 | Horrom et al. | |
| 4,547,505 A | 10/1985 | Oepen et al. | |
| 4,879,288 A | 11/1989 | Warawa et al. | |
| 5,753,661 A | 5/1998 | Moltzen et al. | |
| 5,948,437 A | 9/1999 | Parikh et al. | |
| 6,239,134 B1 | 5/2001 | Sabb et al. | |
| 6,372,734 B1 | 4/2002 | Snape | |
| 6,509,036 B2 | 1/2003 | Pather et al. | |
| 7,071,331 B2 | 7/2006 | Diller et al. | |
| 2004/0019039 A1 | 1/2004 | Dorwald et al. | |
| 2005/0014730 A1 | 1/2005 | Carlson et al. | |
| 2005/0026900 A1 | 2/2005 | Goldstein | |
| 2005/0032183 A1 | 2/2005 | Osslund et al. | |
| 2005/0054682 A1 | 3/2005 | Phillips | |
| 2005/0153841 A1 | 7/2005 | Bunt et al. | |
| 2005/0250775 A1 | 11/2005 | Fish et al. | |
| 2006/0217366 A1 | 9/2006 | Davis et al. | |
| 2009/0093460 A1 * | 4/2009 | Davis et al. | 514/211.13 |
| 2009/0093461 A1 * | 4/2009 | Davis et al. | 514/211.13 |
| 2010/0093700 A1 * | 4/2010 | Christoph et al. | 514/211.13 |
| 2011/0136784 A1 * | 6/2011 | Davis et al. | 514/211.11 |
| 2011/0136785 A1 * | 6/2011 | Davis et al. | 514/211.13 |
| 2011/0136786 A1 * | 6/2011 | Davis et al. | 514/211.13 |
| 2011/0144088 A1 * | 6/2011 | Davis et al. | 514/211.13 |
| 2011/0144089 A1 * | 6/2011 | Davis et al. | 514/211.13 |

FOREIGN PATENT DOCUMENTS

| | | |
|---|---|---|
| EP | 0447857 A1 | 9/1991 |
| JP | 5065257 A | 3/1993 |
| WO | WO-2005002586 A1 | 1/2005 |
| WO | 2005072742 | 8/2005 |
| WO | WO-2008079839 A1 | 7/2008 |

OTHER PUBLICATIONS

Warawa, E.J., et al., "Behavioral Approach to Nondyskinetic Dopamine Antagonists: Identification of Seroquel", J. Med. Chem., 2001, vol. 44, pp. 372-389.
Ressler, K.J., et al., "Role of Norepinephrine in the Pathophysiology and Treatment of Mood Disorders", Biol Psychiatry, 1999, vol. 46, pp. 1219-1233.
Caira "Crystalline polymorphism of organic compounds," Topics in Current Chemistry (1998) 198:163-208.

\* cited by examiner

*Primary Examiner* — Brenda Coleman
(74) *Attorney, Agent, or Firm* — Rebecca Barrett

(57) ABSTRACT

11-piperazin-1-yldibenzo[b,f][1,4]thiazepine, compositions thereof, preparations thereof, formulations thereof, prodrugs thereof and pharmaceutical uses thereof.

11 Claims, 7 Drawing Sheets

Related U.S. Application Data

12/520,617, filed as application No. PCT/US2007/088055 on Dec. 19, 2007, now abandoned, application No. 12/726,619, which is a continuation-in-part of application No. PCT/SE2009/050708, filed on Jun. 11, 2009, application No. 12/726,619, which is a continuation-in-part of application No. PCT/SE2009/050709, filed on Jun. 11, 2009.

(60) Provisional application No. 60/737,863, filed on Nov. 18, 2005, provisional application No. 60/737,861, filed on Nov. 18, 2006, provisional application No. 60/737,862, filed on Nov. 18, 2006, provisional application No. 60/737,885, filed on Nov. 18, 2005, provisional application No. 60/870,964, filed on Dec. 20, 2006, provisional application No. 60/896,481, filed on Mar. 22, 2007, provisional application No. 60/870,970, filed on Dec. 20, 2006, provisional application No. 60/870,979, filed on Dec. 20, 2006, provisional application No. 60/870,982, filed on Dec. 20, 2006, provisional application No. 61/061,608, filed on Jun. 14, 2008, provisional application No. 61/061,606, filed on Jun. 14, 2008.

TGA and DSC of Form I

CRYSTALLINE FORMS

RELATED APPLICATIONS

This is a Continuation in Part of U.S. application Ser. No. 12/093,956 filed Oct. 3, 2008, now abandoned which is a national stage application (under 35 U.S.C. 371) of PCT/US2006/061071 filed Nov. 18, 2006 which claims the benefit of U.S. Provisional Application No. 60/737,863 filed Nov. 18, 2005, U.S. application Ser. No. 12/093,952 filed Oct. 23, 2008, now abandoned which is a national stage application (under 35 U.S.C. 371) of PCT/US2006/061069 filed Nov 18, 2006 which claims the benefit of U.S. Provisional Application No. 60/737,861 filed Nov. 18, 2005, U.S. application No. 12/093,954 filed Nov. 21, 2008 now abandoned which is a national stage application (under 35 U.S.C. 371) of PCT/US2006/061070 filed Nov. 18, 2006 which claims the benefit of U.S. Provisional Application No. 60/737,862 filed Nov. 18, 2005, U.S. application Ser. No. 12/093,957 filed Nov. 7, 2008, now abandoned which is a national stage application (under 35 U.S.C. 371) of PCT/US2006/061072 filed Nov. 18, 2006 which claims the benefit of U.S. Provisional Application No. 60/737,885 filed Nov. 18, 2005, U.S. application Ser. No. 12/520,133 filed Jun. 19, 2009, now abandoned which is a national stage application (under 35 U.S.C. 371) of PCT/US2007/088036 filed Dec. 19, 2007 which claims the benefit of U.S. Provisional Application No. 60/870,964 filed Dec. 20, 2006, U.S. application Ser. No. 12/531,717 filed Sep. 17, 2009, now abandoned which is a national stage application (under 35 U.S.C. 371) of PCT/US2008/057808 filed Mar. 21, 2008 which claims the benefit of U.S. Provisional Application No. 60/896,481 filed Mar. 22, 2007, U.S. application Ser. No. 12/520,152 filed Jun. 19, 2009, now abandoned which is a national stage application under 35 U.S.C. 371) of PCT/US2007/088040 filed Dec. 19, 2007 which claims the benefit of U.S. Provisional Application No. 60/870,970 filed Dec. 20, 2006, U.S. application No. 12/520,162 filed Jun. 19, 2009, now abandoned which is a national stage application under 35 U.S.C. 371) of PCT/US2007/088053 filed Dec. 19, 2007 which claims the benefit of U.S. Provisional Application No. 60/870,979 filed Dec. 20, 2006, U.S. application Ser. No. 12/520,167 filed Jun. 19, 2009, now abandoned which is a national stage application (under 35 U.S.C. 371) of PCT/US2007/088055 filed Dec. 19, 2007 which claims the benefit of U.S. Provisional Application No. 60/870,982 filed Dec. 20, 2006, PCT Application No. PCT/SE2009/050708 filed Jun. 11, 2009 which claims the benefit of U.S. Provisional Application No. 61/061,608 filed Jun. 14, 2008 and PCT Application No. PCT/SE2009/050709 filed Jun. 11, 2009 which claims the benefit of U.S. Provisional Application No. 61/061,606 filed Jun. 14, 2008.

FIELD OF THE INVENTION

The present invention is directed to a crystalline form of the pharmaceutical compound 11-piperazin-1-yldibenzo[b,f][1,4]thiazepine, as well as compositions, preparations, formulations, prodrugs and pharmaceutical uses thereof.

BACKGROUND OF THE INVENTION

A goal of antipsychotic drug development has been to develop agents with increased efficacy and safety along with fewer of the side effects commonly associated with the older antipsychotic medications. Quetiapine fumarate is described in U.S. Pat. No. 4,879,288, which is incorporated herein by reference. Quetiapine fumarate is able to treat both the positive (hallucinations, delusions) and negative symptoms (emotional withdrawal, apathy) of psychosis and is associated with fewer neurological and endocrine related side effects compared to older agents. Quetiapine fumarate has also been associated with a reduction in hostility and aggression. Quetiapine fumarate is associated with fewer side effects such as EPS, acute dystonia, acute dyskinesia, as well as tardive dyskinesia. Quetiapine fumarate has also helped to enhance patient compliance with treatment, ability to function and overall quality of life, while reducing recidivism. P. Weiden et al., *Atypical antipsychotic drugs and long-term outcome in schizophrenia*, 11 J. Clin. Psychiatry, 53-60, 57 (1996). Because of quetiapine fumarate's enhanced tolerability profile its use is particularly advantageous in the treatment of patients that are hypersensitive to the adverse effects of antipsychotics (such as elderly patients).

Derivatives of 11-(piperazin-1-yl)dibenzo[b,f][1,4]-thiazepines and related compounds including metabolites of quetiapine were prepared and evaluated in E. Warawa et al. *Behavioral approach to nondyskinetic dopamine antagonists: identification of Seroquel*, 44, J. Med. Chem., 372-389 (2001). Quetiapine metabolism has been reported in C. L. Devane et al. *Clin. Pharmacokinet.*, 40(7), 509-522 (2001) wherein the structure of 11-piperazin-1-yldibenzo[b,f][1,4]thiazepine (see Formula I below) was shown in FIG. 1. This compound was reported by Schmutz et al. in U.S. Pat. No. 3,539,573. This compound has also been used in processes for preparing quetiapine as reported in U.S. Pat. No. 4,879,288. It has now been found that 11-piperazin-1-yldibenzo[b,f][1,4]thiazepine is a circulating metabolite of quetiapine in humans.

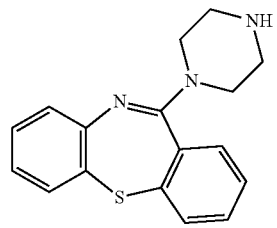

I

Because pharmaceutically active compounds and compositions having, for example, improved properties are consistently sought, there is an ongoing need for improved forms of existing drug molecules. The different properties of crystalline polymorphs of a particular drug are known to influence preparation, formulation, stability, solubility, storage stability, and in vivo pharmacology. Different crystalline forms may be desirable for different types of formulations, different modes of administration, and different indications. For example, stable polymorphs are desirable for facilitating preparation of a drug compound as well as preparation of solid formulations. Accordingly, the crystalline form of 11-piperazin-1-yldibenzo[b,f][1,4]thiazepine described herein address the ongoing needs iterated above.

SUMMARY OF THE INVENTION

The present invention provides crystalline Form A of 11-piperazin-1-yldibenzo[b,f][1,4]thiazepine.

The present invention further provides compositions comprising the crystalline form of the invention.

The present invention further provides methods of preparing the crystalline form of the invention.

The present invention further provides methods of treating at least one symptom or condition associated with schizophrenia and other psychotic disorders, dementia and other cognitive disorders, anxiety disorders, mood disorders, sleep disorders, disorders usually first diagnosed in infancy, childhood, or adolescence and neurodegenerative disorders, comprising administering to a mammal a therapeutically effective amount of a crystalline form of the invention.

DETAILED DESCRIPTION

Figure 1:
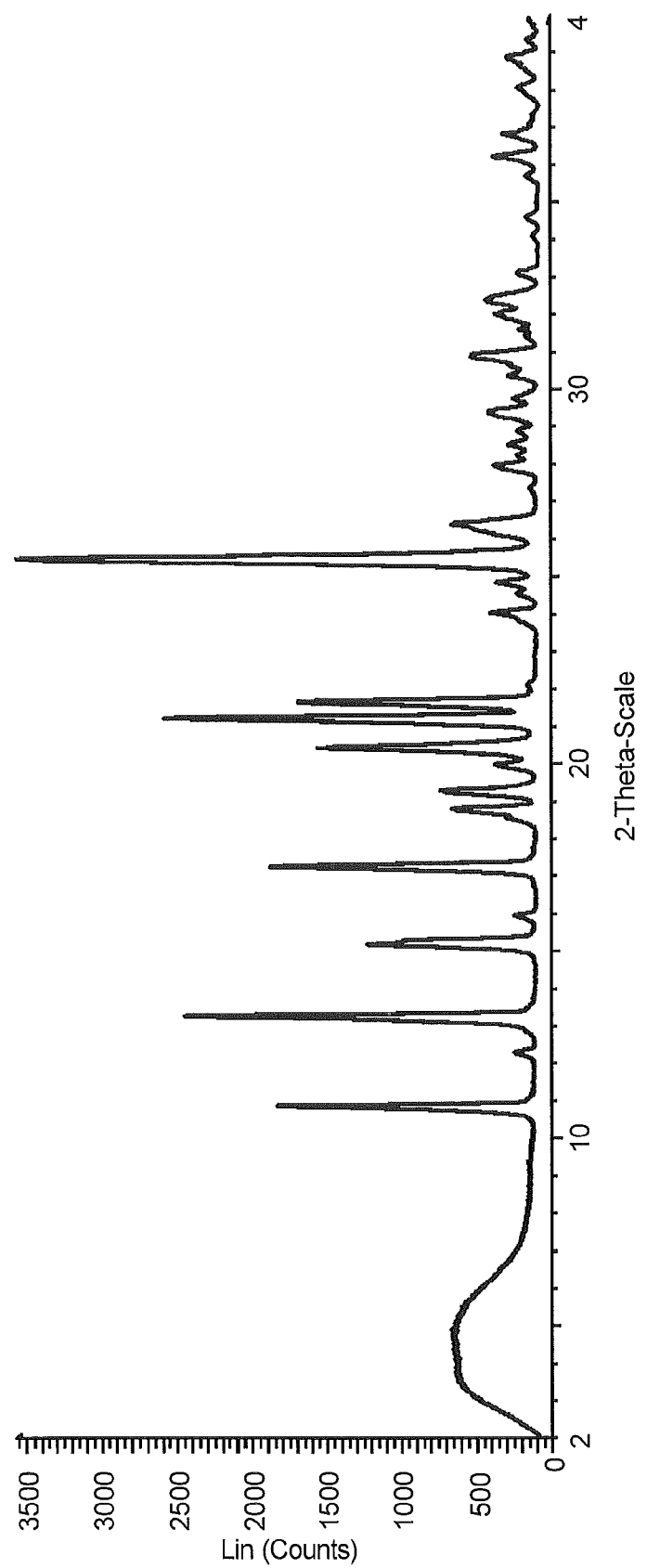
FIG. 1 depicts an X-ray powder diffraction (XRPD) pattern consistent with Form A.

Incorporated by reference in their entirety are Publications US 2009-0069291 A1, (application Ser. No. 12/093,952), US 2010-0025510 A1 (application Ser. No. 12/093,954), US 2009-0215744 A1 (application Ser. No. 12/093,956), US 2009-0069292 A1 (application Ser. No. 12/093,957), WO 2008/879838 (U.S. Counterpart application Ser. No. 12/520,133), WO 2008/116144 (U.S. Counterpart application Ser. No. 12/531,717), US 2010-0016283 A1 (application Ser. No. 12/520,152), US 2010-0016284 (application Ser. No. 12/520,162), US 2010-0056492 (application Ser. No. 12/520,167), WO 2009/151392 (PCT Application PCT/SE2009/050708) and WO 2009/151393 (PCT Application PCT/SE2009/050709).

The compound of Formula I is a dibenzothiazepine that has shown antidopaminergic activity. It has been shown to interact with a broad range of neurotransmitter receptors but has a higher affinity for serotonin (5-HT$_2$) receptors relative to dopamine (D$_2$) receptors in the brain. Preliminary positron emission topography (PET) scans of primate subjects showed that the compound of Formula I reached the brain and occupies D$_1$, D$_2$, 5-HT$_{2A}$, and 5-HT$_{1A}$ receptors and the 5HT Transporter. However, the compound of Formula I was not shown to be efficacious in a mouse standard apomorphine swim test (p.o.) and in a rat D-Ampehtamine locomotor activity test (s.c.).

The compound of Formula I has also been shown to have partial 5HT$_{1A}$ agonist activity and has shown in-vivo efficacy in mouse and rat models for depression. The compound of Formula I may be used as an antipsychotic with a reduction in the potential to cause side effects such as acute dystonia, acute dyskinesia, as well as tardive dyskinesia typically seen with antipsychotics. Results generated from alpha receptor binding data further suggest that the compound of Formula I will have improved tolerability over that of quetiapine and suggest that one would observe a reduced incidence of hypotension. Further the compound of Formula I may be used to treat patients of all ages and is advantageous in the treatment of elderly patients.

The present invention provides, inter alia, a crystalline form of 11-piperazin-1-yldibenzo[b,f][1,4]thiazepine designated as Form A. This crystalline form of 11-piperazin-1-yldibenzo[b,f][1,4]thiazepine can be identified by its unique solid state signature with respect to, for example, X-ray powder diffraction (XRPD), Raman scattering, differential scanning calorimetry (DSC), and other solid state methods. Further characterization with respect to hygroscopicity as well as water or solvent content of the crystalline form can be gauged by any of various routine methods such as thermogravimetric analysis (TGA), dynamic vapor sorption (DVS), DSC and other techniques. For DSC, it is known that the temperatures observed will depend upon the rate of temperature change as well as sample preparation technique and the particular instrument employed. Thus, the values reported herein relating to DSC thermograms can vary by plus or minus about 4° C. For XRPD, the relative intensities of the peaks can vary, depending upon the sample preparation technique, the sample mounting procedure and the particular instrument employed. Moreover, instrument variation and other factors can often affect the 2-theta values. Therefore, the peak assignments of diffraction patterns can vary by plus or minus about 0.2°. XRPD peak data for Form A of 11-piperazin-1-yldibenzo[b,f][1,4]thiazepine is set out in Table A. The corresponding XRPD patterns are provided in FIG. 1.

TABLE A

| Angle 2-Theta ° | Intensity Count | Intensity % |
|---|---|---|
| \multicolumn{3}{c}{(Form A)} |
| 10.8 | 18321 | 51.4 |
| 12.3 | 2390 | 6.7 |
| 13.3 | 24555 | 68.9 |
| 15.2 | 12193 | 34.2 |
| 15.3 | 9799 | 27.5 |
| 16.0 | 2414 | 6.8 |
| 17.2 | 18803 | 52.7 |
| 18.8 | 6502 | 18.2 |
| 19.3 | 7290 | 20.4 |
| 20.0 | 3666 | 10.3 |
| 20.4 | 15535 | 43.6 |
| 21.2 | 25874 | 72.6 |
| 21.7 | 16902 | 47.4 |
| 22.1 | 1473 | 4.1 |
| 24.1 | 3968 | 11.1 |
| 24.2 | 2197 | 6.2 |
| 24.9 | 3579 | 10 |
| 25.5 | 35663 | 100 |
| 26.4 | 6298 | 17.7 |
| 27.9 | 3290 | 9.2 |
| 28.0 | 3746 | 10.5 |
| 28.3 | 2206 | 6.2 |
| 28.6 | 2711 | 7.6 |
| 28.9 | 2142 | 6 |
| 29.4 | 4006 | 11.2 |
| 29.8 | 2464 | 6.9 |
| 30.4 | 2754 | 7.7 |
| 30.9 | 5213 | 14.6 |
| 31.0 | 5143 | 14.4 |
| 31.6 | 2053 | 5.8 |
| 32.1 | 3643 | 10.2 |
| 32.4 | 4234 | 11.9 |
| 32.5 | 3827 | 10.7 |
| 33.2 | 2102 | 5.9 |
| 34.6 | 1540 | 4.3 |
| 35.8 | 1543 | 4.3 |
| 36.3 | 3768 | 10.6 |
| 36.9 | 3086 | 8.7 |
| 38.1 | 2062 | 5.8 |
| 39.0 | 2801 | 7.9 |
| 39.4 | 1492 | 4.2 |

In some embodiments, crystalline Form A of 11-piperazin-1-yldibenzo[b,f][1,4]thiazepine has an X-ray powder diffraction pattern comprising peaks, in terms of 2θ, at about 19.3° and about 25.5°. In further embodiments, the XRPD pattern further comprises a peak, in terms of 2θ, at about 10.8°. In yet a further embodiment, the XRPD pattern further comprises a peak, in terms of 2θ, at about 13.3°. In yet a further embodiment, the XRPD pattern further comprises a peak, in terms of 2θ, at about 15.2°. In yet a further embodiment, the XRPD pattern further comprises a peak, in terms of 2θ, at about 17.2°.

In some embodiments, the XRPD pattern further comprises peaks, in terms of 2θ, at about 10.8°, about 13.3°, about 15.2°, about 17.2°, and about 21.2°. In some embodiments, the XRPD pattern further comprises at least 5 peaks, in terms of 2θ, selected from about 10.8°, about 13.3°, about 15.2°, about 17.2°, about 18.8°, about 19.3°, about 20.4°, about 21.2°, and about 21.7°. In yet further embodiments, the present invention provides a crystalline form (Form A) of 11-piperazin-1-yldibenzo[b,f][1,4]thiazepine having an X-ray powder diffraction pattern substantially as shown in FIG. 1, where the term "substantially" refers variations in intensity and 2-theta values typically observed in the art depending on instrument and sample preparation as described above. It is believed that the broad feature between the 2° and 8° is an instrumental artifact that is not related to Form A.

Figure 2:
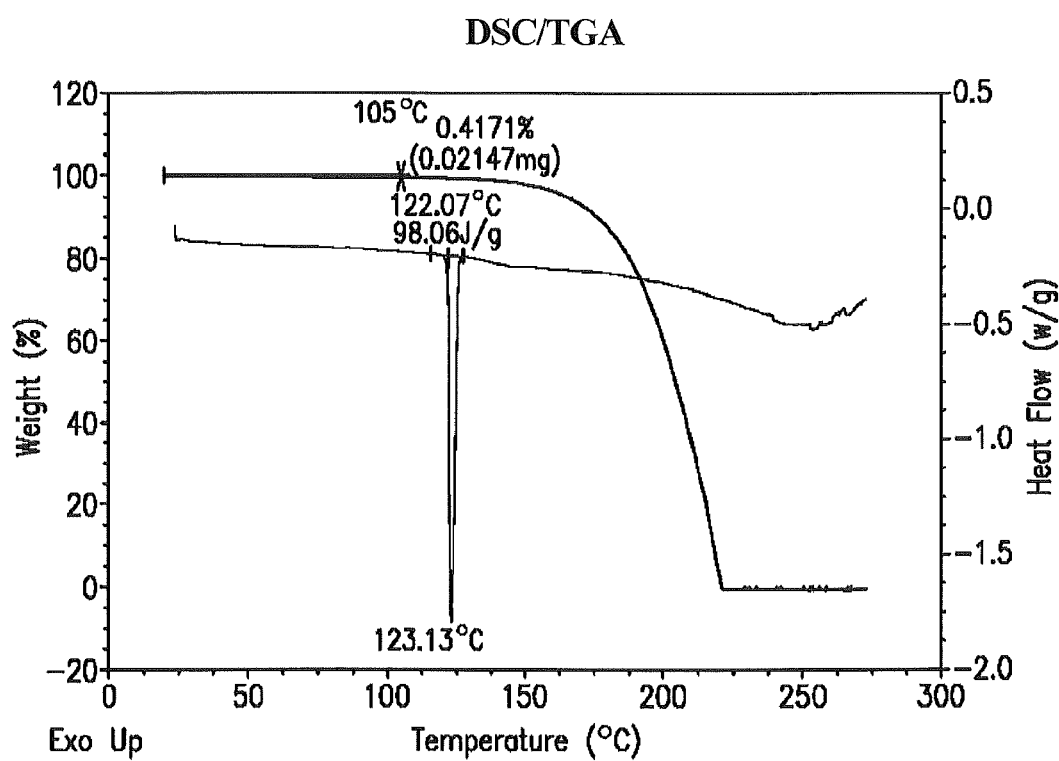
FIG. 2 depicts thermogravimetric analysis (TGA) and differential scanning calorimetry (DSC) data consistent with Form A.

Form A can further be characterized by its differential scanning calorimetry (DSC) thermogram, an example of which is shown in FIG. 2. The thermogram reveals one relatively sharp endotherm peaking at 123° C. which is believed to correspond to a melt event. Thermogravimetric analysis (TGA) of Form A, also shown in FIG. 2, shows about 0.4% weight loss, suggesting the crystalline form is substantially anhydrous and non-solvated. Accordingly, the crystalline form of the invention can have a DSC thermogram and/or TGA substantially as shown in FIG. 2, wherein the term "substantially" in the context of DSC or TGA refers to variations in temperature (e.g., plus/minus about 4° C.), heat flow (e.g., plus/minus about 5%), weight (e.g., plus/minus about 5%) typically observed in the art depending on instrument and sample preparations.

Figure 3:
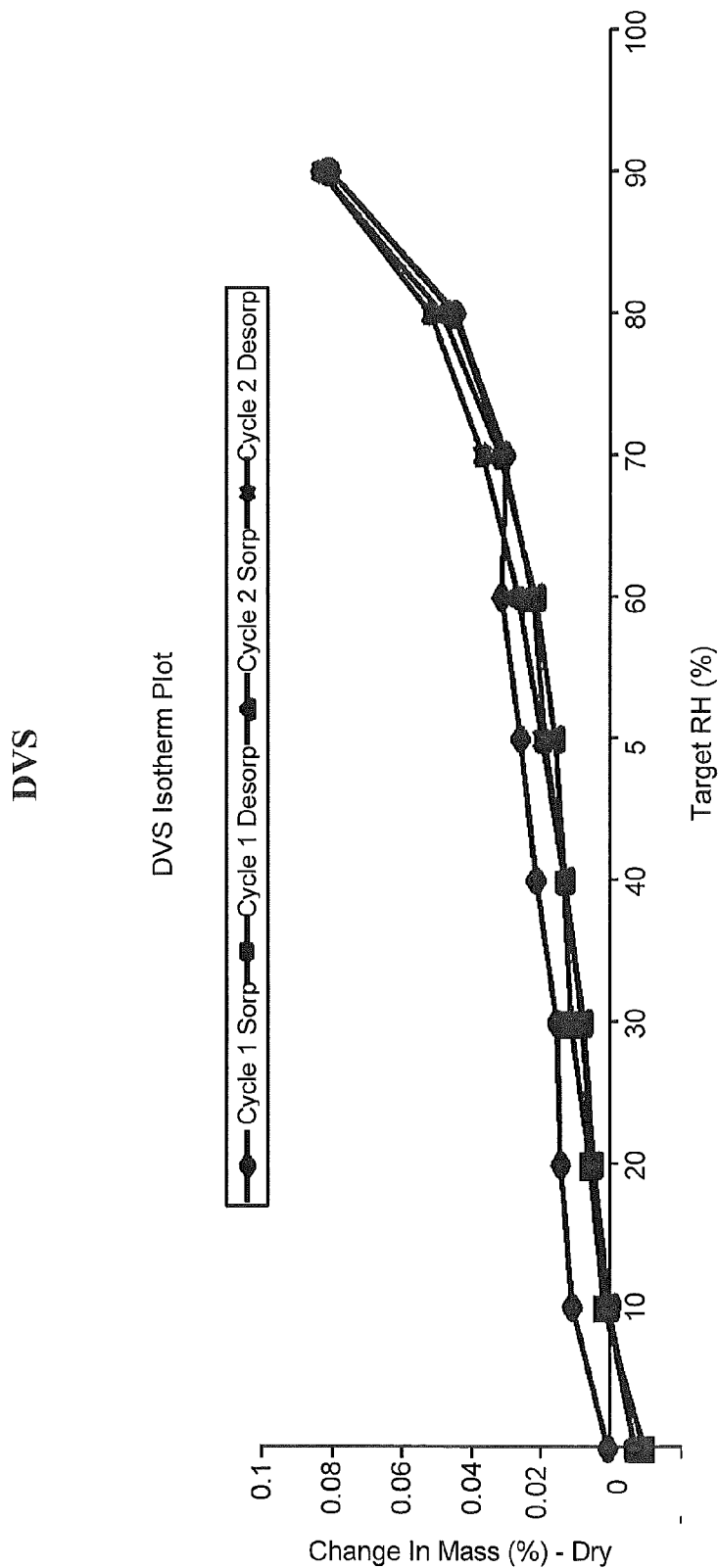
FIG. 3 depicts dynamic vapor sorption (DVS) data consistent with Form A.

Dynamic vapor sorption (DVS) studies of Form A (depicted in FIG. 3) show relatively slight water gain which is reversible without hysteresis, suggesting a substantially non-hygroscopic material. Accordingly, the crystalline form of the invention can have a DVS isotherm plot substantially as shown in FIG. 3, wherein the term "substantially" in the context of DVS refers to variations in RH (e.g., plus/minus about 5%) and mass change (e.g., plus/minus about 5%) typically observed in the art depending on instrument and sample preparations.

The crystalline form of the invention can be prepared by methods routine in the art for preparing various crystalline forms (e.g., polymorphs) of free base small molecules. For example, the crystalline form can be precipitated from a solution containing 11-piperazin-1-yldibenzo[b,f][1,4]thiazepine and a crystallizing solvent. The crystallizing solvent can contain any suitable organic solvent. Example organic crystallizing solvents include ethers such as t-butylmethyl ether, diethyl ether, tetrahydrofuran, dimethoxymethane, 1,3-dioxane, 1,4-dioxane, furan, ethylene glycol dimethyl ether, ethylene glycol diethyl ether, diethylene glycol dimethyl ether, diethylene glycol diethyl ether, triethylene glycol dimethyl ether, anisole, and the like; hydrocarbons such as pentane, hexanes, heptanes, benzene, toluene, and the like; alcohols such as methanol, ethanol, 2-nitroethanol, 2-fluoroethanol, 2,2,2-trifluoroethanol, ethylene glycol, 1-propanol, isopropanol (2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, and the like; nitriles such as acetonitrile or propionitrile; or aldehydes/ketones and ketone-like solvents such as acetone, methylethyl ketone, ethyl acetate, dimethylsulfoxide, dimethylformamide, and the like. The crystallizing solvent can contain one or more of any of the aforementioned organic solvents. The crystallizing solvent can further include water and aqueous mixtures.

The present invention provides, inter alia, a crystalline form of 11-piperazin-1-yldibenzo[b,f][1,4]thiazepine designated as Form I. This crystalline form of 11-piperazin-1-yldibenzo[b,f][1,4]thiazepine can be identified by its unique solid state signature with respect to, for example, X-ray powder diffraction (XRPD), Raman scattering, differential scanning calorimetry (DSC), and other solid state methods. Further characterization with respect to hygroscopicity as well as water or solvent content of the crystalline form can be gauged by any of various routine methods such as thermogravimetric analysis (TGA), dynamic vapor sorption (DVS), DSC and other techniques.

Figure 4:
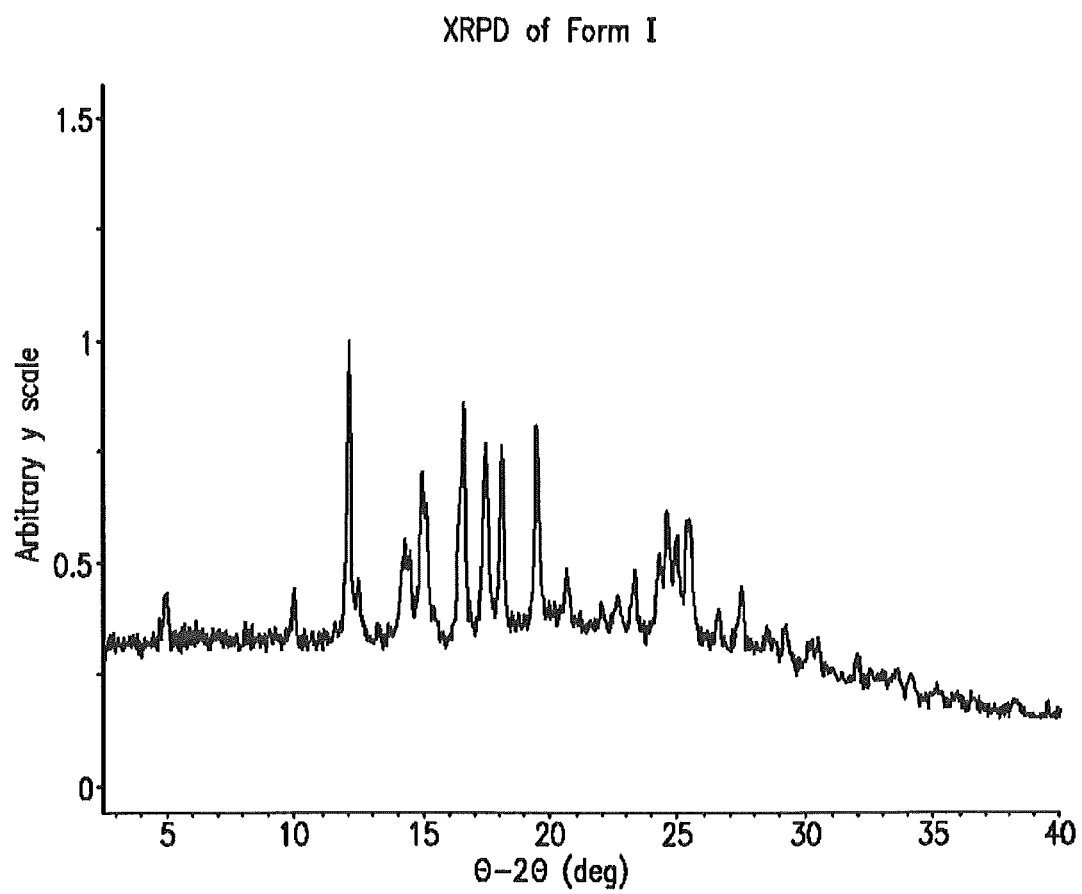
FIG. 4 depicts XRPD pattern consistent with a stable, crystalline polymorph of Form A, labeled Form I.

In some embodiments, the XRPD pattern of Form I further comprises peaks, in terms of 2θ, at about 12°, about 14°, about 15°, about 16.5°, about 17.5° and about 19.5°. In yet further embodiments, the present invention provides a crystalline form (Form I) of 11-piperazin-1-yldibenzo[b,f][1,4]thiazepine having an X-ray powder diffraction pattern substantially as shown in FIG. 4, where the term "substantially" refers variations in intensity and 2-theta values typically observed in the art depending on instrument and sample preparation as described above.

Figure 5:
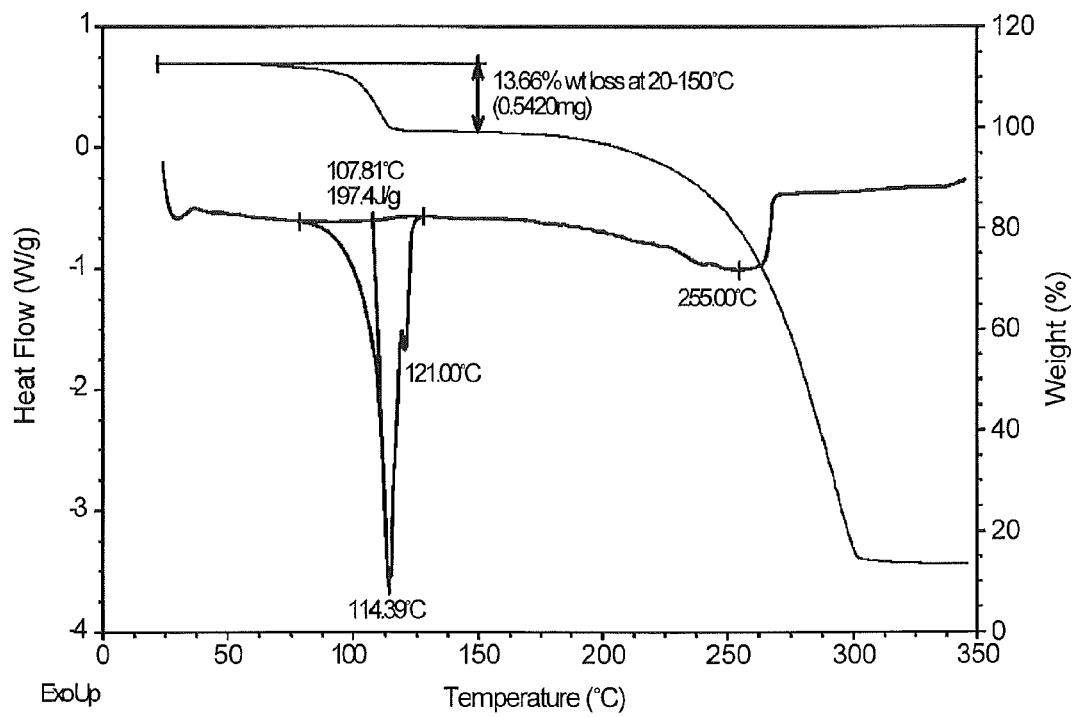
FIG. 5 depicts TGA and DSC data consistent with Form I.

Form I can further be characterized by its differential scanning calorimetry (DSC) thermogram, an example of which is shown in FIG. 5. The thermogram reveals one relatively sharp endotherm peaking between 107 and 108° C. which is believed to correspond to a melt event. FIG. 5 illustrates endotherm at approximately 114° C. and a shoulder at 121° C. likely representing desolvation due to the presence of propanol and water. Thermogravimetric analysis (TGA) of Form I, also shown in FIG. 5, shows about 13.66%. Accordingly, the crystalline form of the invention can have a DSC thermogram and/or TGA substantially as shown in FIG. 5, wherein the term "substantially" in the context of DSC or TGA refers to variations in temperature (e.g., plus/minus about 4° C.), heat flow (e.g., plus/minus about 5%), weight (e.g., plus/minus about 5%) typically observed in the art depending on instrument and sample preparations.

Figure 6:
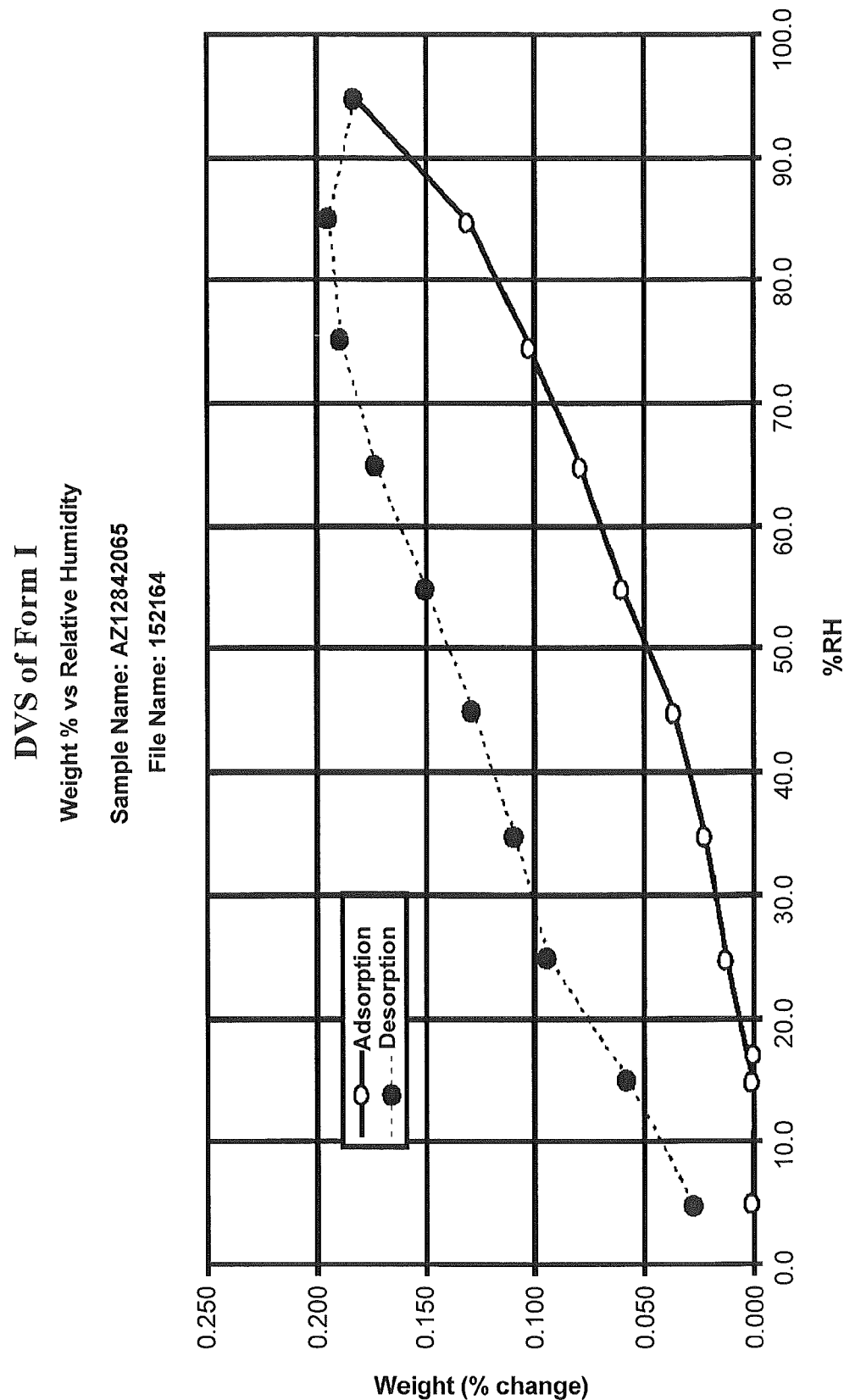
FIG. 6 depicts DVS data consistent with Form I.

Dynamic vapor sorption (DVS) studies of Form I (depicted in FIG. 6) show slight water gain, suggesting the compound is non-hygroscopic. Accordingly, the crystalline form of the invention can have a DVS isotherm plot substantially as shown in FIG. 6, wherein the term "substantially" in the context of DVS refers to variations in RH (e.g., plus/minus about 5%) and mass change (e.g., plus/minus about 5%) typically observed in the art depending on instrument and sample preparations.

Figure 7:
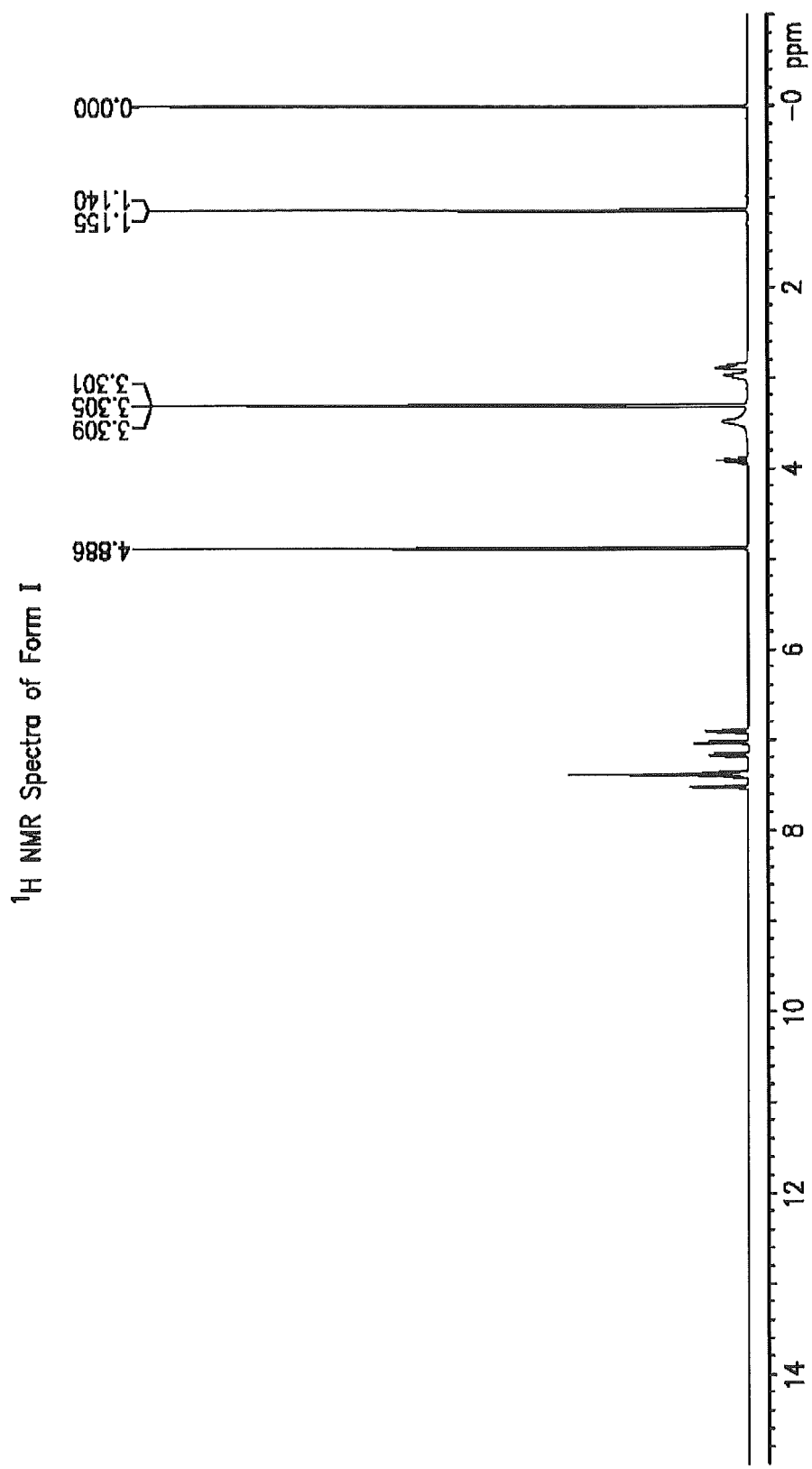
FIG. 7 depicts $^1$H NMR data consistent with Form I.

FIG. 7 depicts proton NMR readings from Form I which are consistent with the predicted structure. The sample contained 0.6 moles of isopropanol that predictably served as a solvent for the precipitation of the crystalline form. Accordingly, the crystalline Form I of the invention can have a proton NMR spectrum substantially as shown in FIG. 7, wherein the term "substantially" in the context of NMR refers to variations in typically observed in the art depending on instrument and sample preparations.

Precipitation of the crystalline form can be induced by any suitable method. Example precipitation methods include evaporation, cooling, and antisolvent methods (e.g., vapor diffusion, layer diffusion, etc.), or combinations thereof.

Other suitable methods of preparing the crystalline forms of the invention include slurrying solid 11-piperazin-1-yldibenzo[b,f][1,4]thiazepine in water, organic solvent (such as any of those listed above), or mixture thereof. Sonication can also be used to induce crystallization.

In some embodiments, Form A can be prepared by precipitation from an organic solvent containing a hydrocarbon solvent such as, for example, toluene. In some embodiments, the organic solvent further contains an ether, such as a high boiling ether like methyl-t-butyl ether. In some embodiments, Form A can be prepared by precipitation from an alcohol solvent such as isopropanol.

Precipitation of Form A can be induced by cooling the solution. For example the solution can be cooled by a total of about 10 to about 40, about 20 to about 50, or about 40 to about 70° C. In some embodiments, the solution is heated to a temperature of about 40 to about 100° C. and then cooled to a temperature of about 30 to about −30° C. In some embodiments, the solution is heated to a temperature of about 50 to about 80° C. and then cooled to a temperature of about 20 to about −10° C. In some embodiments, the solution can be heated to a temperature of about 60 to about 70° C. and then cooled to a temperature of about 10 to about 0° C. Seed crystals of Form A can optionally be added.

In some embodiments, Form A can be prepared by isolating solid 11-piperazin-1-yldibenzo[b,f][1,4]thiazepine from a solution containing a hydrocarbon such as an aromatic hydrocarbon like benzene or toluene and slurrying the solid in a solvent comprising an ether such as a high boiling ether like methyl-t-butyl ether (MTBE).

In some embodiments, Form A can be produced by preparing an aqueous solution of an acid salt (e.g., HCl) of 11-piperazin-1-yldibenzo[b,f][1,4]thiazepine followed by neutralization with a base (e.g., NaOH) to generate the free base; extraction of the free base from the aqueous solution into an organic solvent (e.g., hydrocarbon such as benzene or toluene), and precipitation of Form A from the organic solvent. In some embodiments, the free base can be first isolated from the organic solvent (e.g., by removal of the organic solvent) and then redissolved and/or slurried in a second solvent to yield Form A. In some embodiments, precipitation from the organic solvent or second solvent can be induced by cooling the solution and/or addition of an antisolvent like an ether (e.g., MTBE). In some embodiments, the second solvent is an ether (e.g., MTBE). Further, the organic solvent or second solvent can be optionally seeded with Form A.

The present invention further provides compositions containing the crystalline Form A of 11-piperazin-1-yldibenzo[b,f][1,4]thiazepine described herein. In some embodiments, the compositions of the invention include at least about 50, at least about 60, at least about 70, at least about 80, at least about 90, at least about 95, at least about 96, at least about 97, at least about 98, or at least about 99% by weight of Form A. In some embodiments, compositions of the invention include Form A and a pharmaceutically acceptable carrier.

In further embodiments, the pharmaceutical composition includes up to about 750 mg of the crystalline form of the invention, particularly from about 75 mg to about 750 mg. In another embodiment, the pharmaceutical composition comprises from about 1 mg to about 600 mg of the crystalline form of the invention. In a further embodiment, the pharmaceutical composition contains from about 100 mg to about 400 mg per day of the crystalline form of the invention.

In further embodiments, the pharmaceutical composition includes the crystalline form of the invention in combination with a pharmaceutically acceptable carrier and at least one further active ingredient. Example further active ingredients include benzodiazepines, 5-$HT_{1A}$ ligands, 5-$HT_{1B}$ ligands, 5-$HT_{1D}$ ligands, mGluR2A agonists, mGluR5 antagonists, antipsychotics, NK1 receptor antagonists, antidepressants, or serotonin reuptake inhibitors.

The pharmaceutical compositions of the invention can accordingly be obtained by conventional procedures using conventional pharmaceutical excipients. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. Pharmaceutical compositions intended for oral use can further contain, for example, one or more coloring, sweetening, flavoring and/or preservative agents.

The composition of the invention can be administered by any route including orally, intramuscularly, subcutaneously, topically, intranasally, intraperitoneally, intrathoracially, intravenously, epidurally, intrathecally, intracerebroventricularly and by injection into the joints.

The amount of active ingredient that is combined with one or more excipients to produce a single dosage form will necessarily vary depending upon the host treated and the particular route of administration. The size of the dose for therapeutic or prophylactic purposes of the active compound(s) will naturally vary according to the nature and severity of the symptoms or conditions, the age and sex of the animal or patient and the route of administration, according to well known principles of medicine.

The present invention further provides methods of treating at least one symptom or condition associated with schizophrenia and other psychotic disorders (e.g., psychotic disorder, psychosis); dementia and other cognitive disorders, anxiety disorders (e.g., generalized anxiety disorder); mood disorders (e.g., depressive disorders, major depressive disorders; bipolar disorders including bipolar I and II, bipolar mania, bipolar depression); sleep disorders; disorders usually first diagnosed in infancy, childhood, or adolescence (e.g., attention-deficit disorder and disruptive behavior disorders); and neurodegenerative disorders comprising administering to a mammal a pharmaceutically effective amount of a crystalline form of the invention or composition containing one or more of the same. In some embodiments, the symptoms and conditions include but are not limited to anxiety, agitation, hostility, panic, eating disorders, affective symptoms, mood symptoms, negative and positive psychotic symptoms commonly associated with psychosis and neurodegenerative disorders. In some embodiments, the symptoms and conditions are any of psychosis, schizophrenia, bipolar I, and anxiety.

In some embodiments, the present invention further provides methods of treating at least one symptom or condition associated with but not limited to: 1) Schizophrenia and other Psychotic Disorders including but not limited to Psychotic Disorder, Schizophreniform Disorder, Schizoaffective Disorder, Delusional Disorder, Brief Psychotic Disorder, Shared Psychotic Disorder, and Psychotic Disorder Due to a General Medical Condition; 2) Dementia and other Cognitive Disorders; 3) Anxiety Disorders including but not limited to Panic Disorder Without Agoraphobia, Panic Disorder With Agoraphobia, Agoraphobia Without History of Panic Disorder, Specific Phobia, Social Phobia, Obsessive-Compulsive Disorder, Postraumatic Stress Disorder, Acute Stress Disorder, Generalized Anxiety Disorder and Generalized Anxiety Disorder Due to a General Medical Condition; 4) Mood Disorders including but not limited to a) Depressive Disorders, including but not limited to Major Depressive Disorder and Dysthymic Disorder and b) Bipolar Depression and/or Bipolar mania including but not limited to Bipolar I Disorder, including but not limited to those with manic, depressive or mixed episodes, and Bipolar II Disorder, c) Cyclothymic Disorder, d) Mood Disorder Due to a General Medical Condition; 5) Sleep Disorders; 6) Disorders Usually First Diagnosed in Infancy, Childhood, or Adolescence including but not limited to Mental Retardation, Learning Disorders, Motor Skills Disorder, Communication Disorders, Pervasive Developmental Disorders, Attention-Deficit and Disruptive Behavior Disorders, Feeding and Eating Disorders of Infancy or Early Childhood, Tic Disorders, and Elimination Disorders; 7) Substance-Related Disorders including but not limited to Substance Dependence, Substance Abuse, Substance Intoxication, Substance Withdrawal, Alcohol-Related Disorders, Amphetamine (or Amphetamine-Like)-Related Disorders, Caffeine-Related Disorders, Cannabis-Related Disorders, Cocaine-Related Disorders, Hallucinogen-Related Disorders, Inhalant-Related Disorders, Nicotine-Related Disorders, Opioid-Related Disorders, Phencyclidine (or Phencyclidine-Like)-Related Disorders, and Sedative-, Hypnotic- or Anxiolytic-Related Disorders; 8) Attention-Deficit and Disruptive Behavior Disorders; 9) Eating Disorders; 10) Personality Disorders including but not limited to Obsessive-Compulsive Personality Disorder; and 11) Impulse-Control Disorders, by administering to a patient a pharmaceutically effective amount of a formulation described herein.

The present invention further provides methods of treating at least one symptom or condition described herein by administering to a mammal a pharmaceutically effective amount of a crystalline form of the invention and a therapeutically effective amount of at least one other therapeutically active agent selected from benzodiazepines, 5-HT$_{1A}$ ligands, 5-HT$_{1B}$ ligands, 5-HT$_{1D}$ ligands, mGluR2A agonists, mGluR5 antagonists, antipsychotics, NK1 receptor antagonists, antidepressants, serotonin reuptake inhibitors, and mood stabilizers.

Exemplary benzodiazepines include but are not limited to adinazolam, alprazolam, bromazepam, clonazepam, chlorazepate, chlordiazepoxide, diazepam, estazolam, flurazepam, balezepam, lorazepam, midazolam, nitrazepam, oxazepam, quazepam, temazepam, triazolam and equivalents thereof.

Exemplary 5-HT$_{1A}$ and/or 5HT$_{1B}$ ligands include but are not limited to buspirone, alnespirone, elzasonan, ipsapirone, gepirone, zopiclone and equivalents thereof.

Exemplary mGluR2 agonists may include (1S,3R)-1-aminocyclopentane-1,3-dicarboxylic acid, (2S,3S,4S)alpha-(carboxycyclopropyl)glycine, and 3,5-dihydroxyphenylglycine.

Exemplary antidepressants include but are not limited to maprotiline, amitriptyline, clomipramine, desipramine, doxepin, imipramine, nortryptyline, protriptyline, trimipramine, SSRIs and SNRIs such as fluoxetine, paroxetine, citalopram, escitalopram, sertraline, venlafaxine, fluoxamine, and reboxetine.

Exemplary antipsychotics include but are not limited to clozapine, risperidone, quetiapine, olanzapine, amisulpride, sulpiride, zotepine, chlorpromazine, haloperidol, ziprasidone, and sertindole.

Exemplary mood stabilizers may include but are not limited to Valproic acid (valproate) and its derivative (e.g. divalproex), lamotrigine, lithium, verapamil, carbamazepine and gabapentin.

Administration of two or more active agents can be carried out in combination, e.g., as part of the same pharmaceutical composition, or separately (e.g., serially or consecutively) as part of an appropriate dose regimen designed to obtain the benefits of combination therapy. The appropriate dose regimen, the amount of each dose of an active agent administered, and the specific intervals between doses of each active agent will depend upon the subject being treated, the specific active agent being administered and the nature and severity of the specific disorder or condition being treated.

In general, the crystalline forms of the invention, when used as either a single active agent or when used in combination with another active agent, can be administered to a mammal in an amount up to about 750 mg per day, particularly from about 75 mg to 750 mg per day, in single or divided doses. In another aspect of the invention, the crystalline forms of the invention may be administered in amount from about 1 mg to about 600 mg per day. In a further aspect of the invention, the crystalline form of the invention may be administered in an amount from about 100 mg to about 400 mg per day. Such compounds may be administered on a regimen of up to 6 times per day, preferably 1 to 4 times per day. Variations can occur depending upon the mammal being treated and the individual response to the treatment, as well as on the type of pharmaceutical formulation chosen and the time period and interval at which such administration is carried out. In some instances, dosage levels below the lower limit of the aforesaid range may be more than adequate, while in other cases larger doses may be employed to achieve the desired effect, provided that such larger doses are first divided into several small doses for administration throughout the day.

In some embodiments, the crystalline form is administered comprising a predetermined dosage to a mammal between one and four times a day, wherein the predetermined dosage is between 1 mg and 600 mg.

The present invention also provides a method of treating the symptoms or conditions provided herein comprising the step of administering an initial predetermined dosage of the crystalline form to a human patient twice a day, wherein the predetermined dosage is between 1 mg and 30 mg with increases in increments of 1-50 mg twice daily on the second and third day as tolerated. Thereafter, further dosage adjustments can be made at intervals of 2 days or greater.

A clinician may determine the effective amount by using numerous methods already known in the art. The term "treating" within the context of the present invention encompasses to administer an effective amount of the crystalline form of the present invention, to mitigate either a pre-existing disease state, acute or chronic, or a recurring symptom or condition. This definition also encompasses prophylactic therapies for prevention of recurring conditions and continued therapy for chronic disorders.

The term "mammal" is meant to refer to any warm-blooded animal, preferably a human. In some embodiments, the mammal is in need of treatment because it is suffering from or prone to developing one or more of the symptoms, diseases or disorders described above.

Any or all of the crystalline forms described herein, including any combination thereof, can be used in the preparation of a medicament for the treatment of any of the diseases, disorders, or conditions described herein.

In order that the invention disclosed herein may be more efficiently understood, examples are provided below. It should be understood that these examples are for illustrative purposes only and are not to be construed as limiting the invention in any manner.

EXAMPLES

Example 1

Preparation of
11-piperazin-1-yldibenzo[b,f][1,4]thiazepine Form A

Preparation A

Aqueous solution (584 mL; e.g., prepared by extraction of 11-piperazin-1-yldibenzo[b,f][1,4]thiazepine into water/HCl from a toluene solution such as described below in Preparation B) containing 11-piperazin-1-yldibenzo[b,f][1,4]thiazepine hydrochloride was charged to a jacketed 1 L flask. The flask was then charged with toluene (500 mL) and sodium hydroxide (48% w/w, 33.0 g). The mixture was stirred at 70° C. for 30 minutes and became white and cloudy. The mixture was then allowed to settle for 30 min and the phases were separated. The toluene layer was washed at 70° C. with 2×100 mL of water ($1^{st}$ wash=pH 10.3; $2^{nd}$ wash=pH 8.0). The final toluene volume was 560 mL containing about 74 g of 11-piperazin-1-yldibenzo[b,f][1,4]thiazepine in good purity.

The above procedure was repeated for an additional four aqueous solutions of 11-piperazin-1-yldibenzo[b,f][1,4]thiazepine hydrochloride and the five resulting toluene solutions were combined and evaporated to dryness on a rotary evaporator. The resulting hard solid was then charged to a jacketed vessel and slurried with methyl-t-butyl ether (MTBE) (500 mL). The resulting slurry was stirred overnight at ambient temperature and then cooled to 5° C. and held for 4 h. The solid 11-piperazin-1-yldibenzo[b,f][1,4]thiazepine product was isolated on a no. 3 sinter and washed with 200 mL of cold MTBE. The cake was dried in a vacuum oven overnight at 60° C. yielding 373 g of product.

Preparation B

A toluene solution of 11-piperazin-1-yldibenzo[b,f][1,4] thiazepine (1500 mL, 0.686 mol) prepared by reaction of piperazine with 11-chloro-dibenzo[b,f][1,4]-thiazepine in toluene (see, e.g., U.S. Pat. No. 4,879,288) was treated with 1500 mL deionized water and 90 mL of HCl (32% w/w). The resulting mixture was heated to 70° C. and agitated for 45 min. Agitation was ceased and the mixture allowed to settle and phase-separate for 30 min. The lower aqueous phase, containing the HCl salt of 11-piperazin-1-yldibenzo[b,f][1, 4]thiazepine was isolated. The aqueous phase was then treated with 1000 mL of toluene and 99 g of aqueous NaOH (47% w/w). The resulting mixture was heated to 70° C. and agitated for 45 min. Agitation was ceased and the mixture allowed to settle and phase separate for 30 min. The lower aqueous phase was discarded and the upper organic phase retained to which 300 mL of deionized water was added. The resulting mixture was agitated for 15 min and then allowed to settle for 30 min. The aqueous phase was discarded and the organic phase retained. The organic phase was extracted once more with 300 mL of deionized water. About 750 mL of toluene from the organic phase was distilled out. The resulting concentrate was cooled to 60° C., then 200 mL of methyl-t-butyl ether (MTBE) was added. The resulting mixture was cooled to ambient temperature then seeded with Form A seed crystals. The seeded mixture was then cooled to 10° C. and held at this temperature for 3 hours under slow agitation. The resulting solid was isolated under suction via a no. 3 sinter. The solid product was then washed with 170 mL of MTBE at ambient temperature and dried at 40° C. under vacuum resulting in 175 g (86.4%) of crystalline product. Assay by NMR 95.1% w/w.

Solid 11-piperazin-1-yldibenzo[b,f][1,4]thiazepine (30 g, 0.1016 mol) prepared as described above was slurried in isopropanol (120 mL). The resulting mixture was warmed to about 63-64° C. to completely dissolve the solid. The resulting solution was filtered through a preheated (about 55° C.) split Buchner funnel fitted with filter paper with a pore size of 6 µm. The filtered solution was then adjusted to 55° C. and seeded with seed crystals of Form A (0.024 g). The seeded solution was maintained at 55° C. for about 2 h then linearly cooled to 40° C. over the course of 6 h, linearly cooled to 20° C. over the course of 2 h, and then linearly cooled to 0° C. over the course of 1 h. The resulting slurry was held at 0° C. for 12 h and the filtered to give a solid product cake (13 mm high×68 mm diameter). The product cake was displacement washed with 30 mL isopropanol prechilled to 0° C. and the cake allowed to deliquor. The product was then dried at 40° C. under vacuum yielding 24.9 g (83%) of Form A. Assay by NMR: 98.9% w/w.

Example 2

Properties of Form A

Individual samples of Form A were slurried in various solvents (acetone, ethanol, ethyl acetate, methylethyl ketone, toluene, and water). The mixtures were stirred overnight at room temperature in sealed containers. The samples were then filtered and vacuum dried at 50° C. for 2 h. The resulting material in each of the solvents tested was a white crystalline material having an XRPD diffraction pattern consistent with Form A. Accordingly, Form A maintained in a variety of solvents and workup conditions.

Example 3

Thermal Analysis of Form A

DSC and TGA data consistent with Form A are provided in FIG. 2. The DSC data displayed one sharp endothermic event at 123.1° C. which corresponded to a melt event prior to degradation. The TGA data shows 0.4% weight loss in the water/solvent region.

Example 4

Dynamic Vapor Sorption Analysis of Form A

DVS data of Form A revealed that the crystalline form is non-hygroscopic showing only slight, reversible water gain without hysteresis. As shown in FIG. 3, two cycles overlay well with no evidence of form change.

Example 5

Properties of Form I

Individual samples of Form I were prepared during crash cooling experiments conducted in isopropanol. The mixture was placed at 60° C. and then transferred quickly to freezer at −20° C. Several crash cooling experiments were set up to reproduce and scale up Form I for further characterization.

Only one experiment yielded Form I, the other attempts resulted in Form A. The samples were then filtered and vacuum dried for 2 h. The resulting material in isopropanol was a white crystalline material having an XRPD diffraction pattern consistent with FIG. 4. Accordingly, Form I maintained in isopropanol and workup conditions. It remained unchanged after drying in air overnight and in a vacuum oven at ambient temperature for three days.

Example 6

Thermal Analysis of Form I

DSC and TGA data consistent with Form I are provided in FIG. 5. The DSC data displayed one sharp endotherm peaking at approximately 108° C., which is believed to correspond to a melt event. FIG. 5 also illustrates endotherm at approximately 114° C. and a shoulder at 121° C. likely representing desolvation due to the presence of propanol and water. The TGA data shows 13.66% weight loss in the water/solvent region.

Example 7

Dynamic Vapor Sorption Analysis of Form I

DVS data of Form I revealed that the crystalline form is non-hygroscopic. Moisture sorption/desorption data are shown in FIG. 6. An insignificant weight gain of 0.2% was observed from 5 to 95% RH. All of this weight was lost on re-equilibration at 5% RH. The post-moisture balance XRPD was identical to that of the starting material. Based on these data, Form I is non-hygroscopic.

Example 8

Proton Nuclear Magnetic Resonance Analysis of Form I

The newly prepared Form I material was analyzed by proton NMR. Based on the NMR data, it contained approximately 0.6 mole of isopropanol. The $^1$H NMR spectrum is presented in FIG. 7 and is consistent with the compound structure.

Example 9

Instrument Parameters

The XRPD, DSC, TGA, and $^1$H NMR data provided herein were collected according to the instrument parameters provided below.

| XRPD | |
|---|---|
| Instrument | Bruker D8 Discover |
| Scan range | 2-40° 2θ |
| Step size | 0.007° 2θ |
| Scan speed | 0.2 sec/step |
| Scan type | 2TH/T |
| Lamp intensity | 35 kV/45 mA |
| TGA | |
| Instrument | TA Instruments Model 2950 |
| Ramp speed | 2° C./min |
| Temperature range | RT to 275° C. |
| DSC | |
| Instrument | TA Instruments Model 2920 |
| Temperature range | 25° C. to 275° C. |
| Ramp speed | 2° C./min |
| NMR | |
| Instrument | Varian $^{UNITY}$ INOVA-400 spectrometer |
| Temperature range | ambient temperature |
| $^1$H Larmor frequency | 399.803 MHz |
| $^1$H pulse width | 8.2 or 7.1 µs |
| Acquisition time | 2.50 seconds |
| Reference | internal tetramethylsilane (TMS) at 0.0 ppm |

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A crystalline form (Form A) of 11-piperazin-1-yldibenzo[b,f][1,4]thiazepine having an X-ray powder diffraction pattern comprising peaks, in terms of 2θ, at about 19.3° and about 25.5°.

2. The crystalline form of claim 1 further comprising peaks, in terms of 2θ, at about 10.8°, about 13.3°, about 15.2°, about 17.2°, and about 21.2°.

3. The crystalline form of claim 1 further comprising at least 5 peaks, in terms of 2θ, selected from about 10.8°, about 13.3°, about 15.2°, about 17.2°, about 18.8°, about 19.3°, about 20.4°, about 21.2°, and about 21.7°.

4. The crystalline form of claim 1 having an X-ray powder diffraction pattern substantially as shown in FIG. 1.

5. The crystalline form of claim 1 having a differential scanning calorimetry thermogram comprising an endotherm at about 123° C.

6. The crystalline form of claim 1 having a differential scanning calorimetry trace substantially as shown in FIG. 2.

7. The crystalline form of claim 1 which is substantially non-hygroscopic.

8. The crystalline form of claim 1 having a dynamic vapor sorption cycle substantially as shown in FIG. 3.

9. The crystalline form of claim 1 having a thermogravimetric analysis profile substantially as shown in FIG. 2.

10. A method of preparing the crystalline form of claim 1 comprising crystallizing said crystalline form from a solution comprising 11-piperazin-1-yldibenzo[b,f][1,4]thiazepine and a solvent comprising a hydrocarbon or an alcohol.

11. The method of claim 10 wherein said hydrocarbon is toluene and said alcohol is isopropanol.

* * * * *